US011202924B2

(12) United States Patent
Gagneur et al.

(10) Patent No.: US 11,202,924 B2
(45) Date of Patent: Dec. 21, 2021

(54) SINGLE ALIGNMENT ASSORTED PROCEDURES PHANTOM FOR LINEAR ACCELERATOR QUALITY ASSURANCE IN RADIATION ONCOLOGY

(71) Applicant: Mayo Foundation for Medical Education and Research, Rochester, MN (US)

(72) Inventors: Justin D. Gagneur, Phoenix, AZ (US); Michael D. Armstrong, Scottsdale, AZ (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 0 days.

(21) Appl. No.: 16/705,794

(22) Filed: Dec. 6, 2019

(65) Prior Publication Data
US 2020/0179723 A1    Jun. 11, 2020

Related U.S. Application Data

(60) Provisional application No. 62/776,948, filed on Dec. 7, 2018.

(51) Int. Cl.
*A61N 5/10*    (2006.01)

(52) U.S. Cl.
CPC .... *A61N 5/1075* (2013.01); *A61N 2005/1076* (2013.01)

(58) Field of Classification Search
CPC .................. A61N 5/1075; A61N 2005/1076

USPC ............... 250/492.1, 492.2, 492.3; 600/1
See application file for complete search history.

(56) References Cited

U.S. PATENT DOCUMENTS

| 7,349,523 | B2 | 3/2008 | Jenkins |
| 7,594,753 | B2 | 9/2009 | Main |
| 8,845,191 | B2 | 9/2014 | Ngar |
| 2016/0166857 | A1 | 6/2016 | Nelms |
| 2017/0122885 | A1* | 5/2017 | Van Stevendaal ... G01N 23/041 |

FOREIGN PATENT DOCUMENTS

WO    2017200834 A1    11/2017

OTHER PUBLICATIONS

American College of Radiology. 2014. ACR-AAPM Technical Standard Medical Physics Performance Monitoring of Image-Guided Radiation Therapy (IGRT). Resolution 36. Revised 2014.
American College of Radiology. 2015. ACR-AAPM Technical Standard for the performance of Radiation Oncology Physics for External Beam Therapy. Resolution 52. Revised 2015.
(Continued)

*Primary Examiner* — Nicole M Ippolito
(74) *Attorney, Agent, or Firm* — Quarles & Brady LLP

(57) ABSTRACT

Described here is a phantom for use in quality assurance ("QA") of a radiation treatment system, such as a linear accelerator ("LINAC"). The QA phantoms described in the present disclosure enable the implementation of a number of different technical standards with a single phantom. For instance, the QA phantom described in the present disclosure can replace five separate pieces of equipment and four unique setups with a single phantom and a single setup. To this end, the QA phantom can be referred to as a single alignment assorted procedures ("SNAP") phantom.

23 Claims, 6 Drawing Sheets

(56) References Cited

OTHER PUBLICATIONS

Best Medical. Best Particle Therapy Ion Rapid Cycling Medical Synchrotron (IRMCS) Brochure. Accessed online at http://www.bestmedical.com/news/JACMP_July25_to_Aug21_2018_JACMP_BPT_PTCOG.pdf. Jul. 25, 2018.

CIRS ISO Cube Daily QA Phantom webpage. Accessed online at: http://www.cirsinc.com/products/modality/1/iso-cube-daily-qa-phantom/. Archive version dated Nov. 9, 2017.

Halvorsen, P. H., et al. "AAPM-RSS medical physics practice guideline 9. a. for SRS-SBRT." Journal of applied clinical medical physics 18.5 (2017): 10-21.

IBA Dosimetry, myQA Daily. Accessed online at: https://www.iba-dosimetry.com/product/myqa-daily/ on Apr. 14, 2020.

Klein, E. E., et al. "Task Group 142 report: Quality assurance of medical accelerators." Medical physics 36.9Part1 (2009): 4197-4212.

LAP. Easy Cube Webpage. Accessed online at: https://www.lap-laser.com/medical-technology/quality-assurance/easy-cube/ on Apr. 14, 2020.

RadImage RIT trend Brochure. On or before Oct. 17, 2018.

Smith, K., et al. "AAPM Medical Physics Practice Guideline 8. a.: linear accelerator performance tests." Journal of applied clinical medical physics 18.4 (2017): 23-39.

Subramanian, M. et al. Ion Rapid Cycling Medical Synchrotron (IRCMS): Status and Future Plans. 55th Annual Meeting of the Particle Therapy Cooperative Group. Prague, CZ, May 2016.

\* cited by examiner

US 11,202,924 B2

SINGLE ALIGNMENT ASSORTED PROCEDURES PHANTOM FOR LINEAR ACCELERATOR QUALITY ASSURANCE IN RADIATION ONCOLOGY

CROSS-REFERENCE TO RELATED APPLICATIONS

This application claims the benefit of U.S. Provisional Patent Application Ser. No. 62/776,948, filed on Dec. 7, 2018, and entitled "SINGLE ALIGNMENT ASSORTED PROCEDURES (SNAP) PHANTOM FOR LINEAR ACCELERATOR QUALITY ASSURANCE IN RADIATION ONCOLOGY," which is herein incorporated by reference in its entirety.

BACKGROUND

The American College of Radiology ("ACR") and the American Association of Physicists in Medicine ("AAPM") have multiple different technical standards that are commonly used for quality assurance ("QA") of a radiation treatment system, such as those implementing a linear accelerator ("LINAC"). These can include the following five technical standards, which are common, but non-limiting examples: AAPM Task Group 142, AAPM Medical Physics Practice Guideline 8, AAPM Medical Physics Practice Guideline 9m ACR-AAPM Technical Standard for the Performance of Radiation Oncology Physics for External Beam Therapy, and ACR-AAPM Technical Standard for Medical Physics Performance Monitoring of Image-Guided Radiation Therapy ("IGRT").

In routine practice, implementing these or other technical standards requires the use of multiple different phantoms in a number of different setups to properly test the QA of the radiation treatment system. This is an inefficient and costly practice.

SUMMARY OF THE DISCLOSURE

The present disclosure addresses the aforementioned drawbacks by providing a phantom for quality assurance of a radiation treatment system. The phantom includes a body having a top surface and a bottom surface. The body extends from the top surface to the bottom surface to define a volume. The top surface is sloped relative to the bottom surface, and the body is composed of a radiotransparent material. A plurality of markings are on the top surface of the body, including a center marking located at a center of the top surface, an offset marking that is offset from the center marking, and a field-of-view marking centered about the center marking and demarcating a field-of-view verification area for a light field of a radiation treatment system. A plurality of isocenter alignment markers are also arranged on an edge of the body. A plurality of radiopaque markers are also arranged within the volume of the body, including an isocenter marker arranged within the volume of the body and centered with respect to the center marking and a radiation field-of-view marker arranged about the isocenter marker to demarcate a field-of-view verification area for a radiation field of a radiation treatment system.

It is another aspect of the present disclosure to provide a phantom for quality assurance of a radiation treatment system. The phantom includes a body having a top surface and a bottom surface. The body extends from the top surface to the bottom surface to define a volume. The top surface is sloped relative to the bottom surface in a first direction by a first angle, and relative to the bottom surface in a second direction by a second angle. The body is composed of a radiotransparent material.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
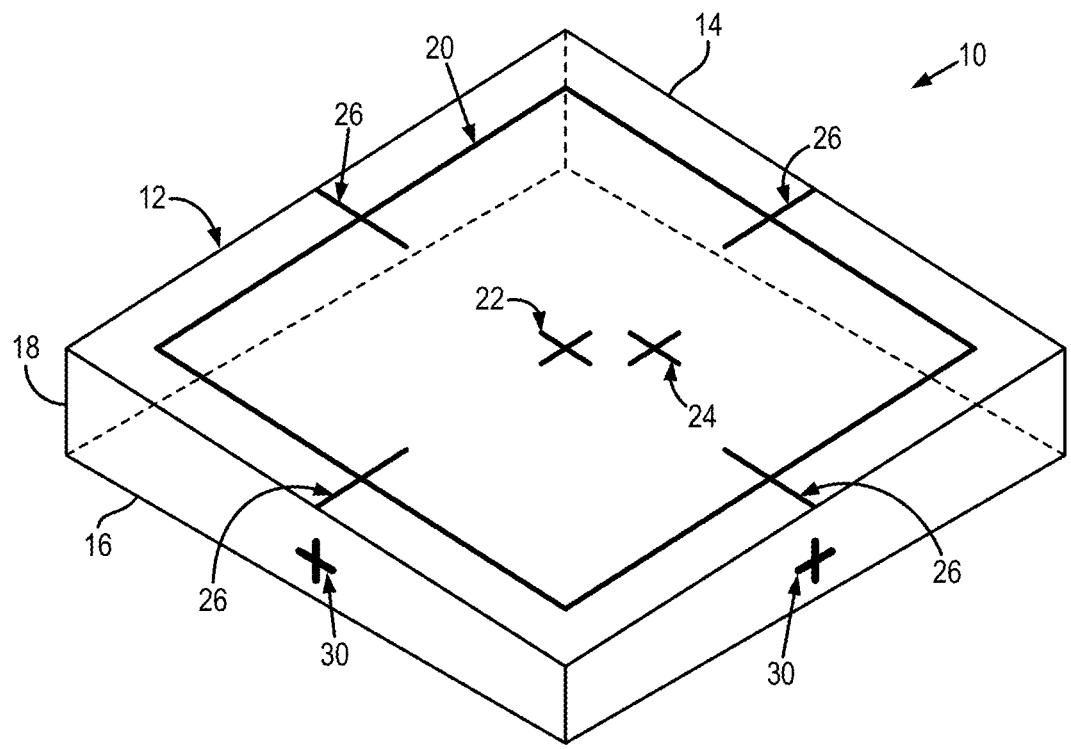
FIG. 1 is a view of an example of a single alignment assorted procedures ("SNAP") phantom for use in radiation treatment system quality assurance ("QA").
Figure 2:
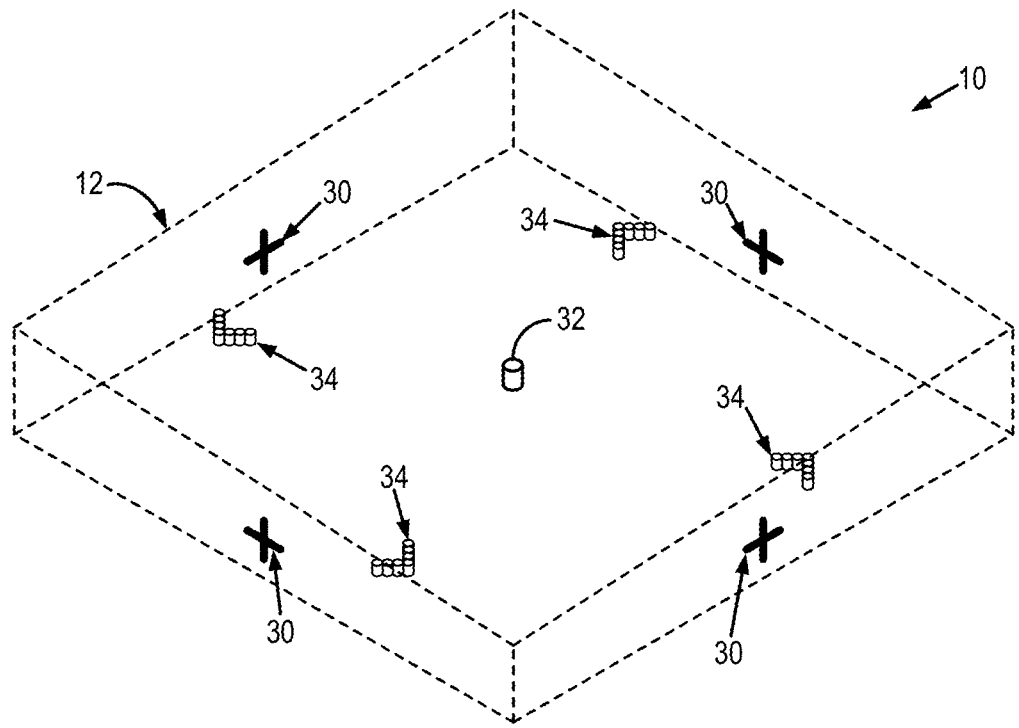
FIG. 2 is a view showing the internal components of the example SNAP phantom of FIG. 1.

Described here is a phantom for use in quality assurance ("QA") of a radiation treatment system, such as a linear accelerator ("LINAC"). Methods for using the QA phantoms are also described.

In general, the QA phantoms described in the present disclosure enable the implementation of a number of different technical standards with a single phantom. To this end, the QA phantom can be referred to as a single alignment assorted procedures ("SNAP") phantom. Whereas incorporating various technical standards into a QA program typically requires multiple different phantoms each requiring different setups, the QA phantoms described in the present disclosure enable the use of a single phantom to implement multiple different technical standards. For instance, the SNAP QA phantom described in the present disclosure can replace five separate pieces of equipment and four unique setups with a single phantom and a single setup. The SNAP QA phantom can be used to test, for example, radiation treatment system performance, absolute table (e.g., treatment couch) position, radiation isocentricity, light versus radiation field (e.g., x-ray) congruence, and table (e.g., treatment couch) pitch/roll accuracy.

By using the SNAP QA phantom described in the present disclosure, a more streamlined QA process with increased cost and time efficiency can be achieved. For instance, the single setup significantly reduces the QA time and allows the medical physicist to be utilized elsewhere in a clinic, or to more efficiently return a repaired radiation treatment system back to clinical service due to the ease of setup and reduced chance of testing error. As an example, using the SNAP QA phantom radiation treatment system performance, absolute table (e.g., treatment couch) position, radiation isocentricity, light versus radiation field (e.g., x-ray) congruence, and table (e.g., treatment couch) pitch/roll accuracy can all be tested in about 10 minutes, which represents a 30-60 minute time saving. Costs can be reduced because the end user only needs to purchase a single piece of equipment—which may be relatively inexpensive—to perform five different tests, as opposed to purchasing five separate pieces of equipment that can traditionally cost several thousands of dollars each.

As shown in FIGS. 1-8, a QA phantom 10 includes a body 12 extending from a top surface 14 to a bottom surface 16 to define a volume of the body 12. Preferably, the body 12 is a solid block of material, but in some instances the body 12 may be at least partially hollow. The outer edge 18 of the body 12 (e.g., the sides of the body 12 extending between the top surface 14 and the bottom surface 16) preferably form a right angle with the bottom surface 16. In some configurations, one or more of the sides may form an angle greater than or less than ninety degrees with the bottom surface 16 of the QA phantom 10 body 12.

In general, the body 12 is composed of a radiotransparent material that is substantially transparent to high energy photons, x-ray, or other radiation, such that there is little to no attenuation of the high energy photons, x-ray, or other radiation. The body 12 can be composed of a plastic or polymer material that is radiotransparent. As one example, the body 12 can be composed of a polylactic acid ("PLA"). As another example, the body 12 could be composed of nylon. In some embodiments, the body 12 can be manufactured using an additive manufacturing process. It will be appreciated that other manufacturing and fabrication processes can also be utilized.

The body 12 of the QA phantom 10 is sized and shaped to be used in connection with a QA program for a radiation treatment system. As one non-limiting example the body 12 can have a square-shaped bottom surface 16 that is large enough to span the light and radiation fields-of-view of the radiation treatment system for which the QA phantom 10 will be used. For instance, the bottom surface 16 can be a 17 cm-by-17 cm square. More generally, the bottom surface 16 can be sized such that the width and length of the bottom surface 16 (or of an area bounding the bottom surface 16 when the bottom surface 16 is shaped as a circle, polygon, or other arbitrary shape) span a desired field-of-view. The width and length can therefore range upwards of 40 cm or more in order to span larger fields-of-view. In other configurations, the bottom surface 16 can have a rectangular shape, a circular shape, another polygonal shape, or any other arbitrary shape. In some configurations, the body 12 of the QA phantom 10 can have an overall height of 6 cm. Alternatively, the height of the body 12 can be less than 6 cm. In other instances, the height of the body 12 may be greater than 6 cm. The height of the body 12 can be selected based on considerations of the slope of the top surface 14 and minimum separation distance between the bottom surface 16 of the QA phantom 10 body 12 and any radiopaque markers arranged within the volume of the body 12.

The top surface 14 is sloped with respect to the bottom surface 16. In general, the slope of the top surface 14 is selected to match the pitch and roll specifications of the patient table for the radiation treatment system for which the QA phantom 10 will be used. In FIGS. 1-8, the top surface 14 of the QA phantom 10 body 12 is shown as having a slope for both the pitch and roll of the treatment couch. In other configurations, the top surface 14 may be sloped with respect to only one of the pitch or the roll of the treatment couch. For instance, the top surface 14 of the QA phantom 10 body 12 can be sloped by a pitch angle measured relative to the pitch axis, a roll angle measured relative to the roll axis, or both. As used herein, the pitch axis corresponds to the y-axis and the roll axis corresponds to the x-axis, where the z-axis is normal to the surface of the treatment couch. Relative to the QA phantom 10, the z-axis is normal to the bottom surface 16 of the QA phantom 10 body 12 (e.g., the height of the QA phantom 10 body is along the z-axis, whereas the length and width of the QA phantom 10 body 12 are along the x-axis and y-axis).

As a non-limiting illustrative example, when the top surface 14 is square-shaped or rectangular-shaped, and is sloped for both pitch and roll, the slope of the top surface 14 will vary along the diagonal of the top surface. When such a top surface 14 is only sloped for pitch or roll, then the slope will vary from one edge of the top surface 14 to the opposite edge.

As one non-limiting example, for a radiation treatment system having six degree of freedom couch min/max specifications, the slope of the top surface 14 can have three degrees of pitch and three degrees of roll. In this example, when the full three degree pitch and roll is applied to the treatment couch, the top surface 14 of the QA phantom 10 will be level when the QA phantom 10 is placed on the treatment couch. The user can then use a level (e.g., a high precision spirit level, a digital level) to assess the mechanical accuracy of the pitch and roll movement of the treatment couch. It will be appreciated by those skilled in the art that the slope of the top surface 14 can be selected to match the min/max specifications of other radiation treatment systems or treatment couches.

As also shown, one or more radiopaque markers are arranged on the QA phantom 10 body 12, within the volume of the body 12, or combinations thereof. In general, the radiopaque markers can be used in connection with various technical standards for a QA program associated with a radiation treatment system. For instance, the radiopaque markers can assist with verifying the isocentricity of the radiation field of the radiation treatment system.

The markings and radiopaque markers can also be used collectively in connection with various technical standards for a QA program associated with a radiation treatment system. For instance, the markings and radiopaque markers can be used to verify alignment of the light field of the radiation treatment system with the radiation field of the radiation treatment system.

As shown, a plurality of markings (e.g., markings 20, 22, 24, 26) are made on the top surface 14 of the QA phantom 10 body 12. In general, the markings can be used in connection with various technical standards for a QA program associated with a radiation treatment system. For instance, the markings can assist with jaw positioning, alignment verifications, and couch shift verifications. In general, the markings can be made with an ink or a dye on the surface of the QA phantom 10 body 12. In other instances, the markings can be stickers or other indicia adhered to or otherwise coupled to the QA phantom 10 body 12. Some or all of the marking may be radiopaque markings. For instance, the markings can be composed of a radiopaque dye or ink applied to the top surface 14 of the body 12.

The top surface 14 can include a field-of-view marking 20 for verification of jaw positioning. As one example, the field-of-view marking 20 can be a 15 cm-by-15 cm square. The top surface 14 can also be marked with a center marking 22 and an offset marking 24. As one example, the center marking 22 can be a crosshair marked on the center of the top surface 14. The offset marking 24 can be a crosshair marked on the top surface 14 offset from the center marking 24. The center marking 22 and the offset marking 24 can be used for couch shift verification.

The top surface 14 can also be marked with laser alignment markings 26 to assist with aligning the QA phantom 10 relative to a laser alignment system associated with the radiation treatment system. As an example, the laser alignment markings 26 can include linear markings on the top surface 14 extending outward from the periphery of the top surface 14 towards the center marking 22.

A plurality of isocenter alignment markers 30 can also be arranged on the outer surface of the body 12 (e.g., on the edge 18 of the body). As an example, the isocenter alignment markers 30 can include crosshair-shaped markers that are arranged on the edge 18 of the QA phantom 10 body 12. The isocenter alignment markers 30 can be manufactured as part of the QA phantom 10 body 12 (e.g., via additive manufacturing). In some instances, the isocenter alignment markers 30 are made to partially protrude from the edge 18 of the QA phantom 10 body 12. The isocenter alignment markers 30 can also be markings or indicia arranged on the surface of the QA phantom 10 body 12, such as markings or indicia on the edge 18 of the body 12. In some configurations, one isocenter marker 30 can be arranged on each side of the QA phantom 10 body 12. The isocenter alignment markers 30 are arranged on the edge 18 of the QA phantom 10 body 12 such that they are coaligned with the isocenter marker 32 described below. In some configurations, the isocenter alignment markers 30 can be partially or fully embedded in the volume of the QA phantom 10 body 12. The isocenter alignment markers 30 can be used for laser alignment with wall-mounted lasers to aid in the alignment of the QA phantom 10. The isocenter alignment markers 30 are preferably composed of a radiotransparent material, such that they do not obscure the isocenter marker 32 when the QA phantom 10 is imaged.

As also shown, one or more radiopaque markers (e.g., radiopaque markers 32, 34) are arranged on or within the body 12 of the QA phantom 10. These radiopaque markers are composed of a radiopaque material that is substantially opaque to high energy photons, x-rays, or other radiation, such that the radiopaque material attenuates or blocks transmission of the high energy photons, x-rays, or other radiation. For example, the radiopaque markers can be composed of steel, ceramic, lead, or a suitable high-Z material.

In some configurations, the radiopaque markers can be compatible with image analysis software (e.g., MATLAB image analysis code or other image analysis software applications) for automatic or semi-automated analysis of images of the QA phantom 10.

The radiopaque markers may include an isocenter marker 32, which may be a spherical or other shaped marker that is aligned with the center marker 22 on the top surface 14 of the QA phantom 10 body 12. In some instances, the isocenter marker 32 is arranged in the center of the volume of the QA phantom 10 body 12. The isocenter marker 32 is sized to be compatible with image analysis software or methods, yet small enough so as not to interfere with the other radiopaque markers. As one example, the isocenter marker 32 can be a spherical or cylindrical marker with a 5 mm diameter. The isocenter marker 32 may, in some instances, be referred to as a Winston-Lutz marker, and may be used for measuring the radiation isocentricity of the radiation treatment system.

The radiopaque markers also include one or more radiation field-of-view ("FOV") markers 34 that are arranged to demarcate a radiation field-of-view verification area for a radiation field of the radiation treatment system for which the QA phantom 10 will be used. Preferably, the radiation FOV verification area demarcated by the radiation FOV markers 34 is aligned with the field-of-view marking 20 on the top surface 14 of the QA phantom 10 body 12, such that alignment of the radiation field-of-view can be verified relative to the light field of the radiation treatment system.

The one or more radiation FOV markers 34 can include a single marker that demarcates all or a portion of the radiation FOV verification area. For instance, the one or more radiation FOV markers 34 can include a radiopaque marker that circumscribes the isocenter marker 30. In other configurations, the one or more radiation FOV markers 34 can include a plurality of markers. In these instances, the radiation FOV markers 34 can be arranged at points or as segments demarcating all or part of the radiation FOV verification area.

Figure 3:
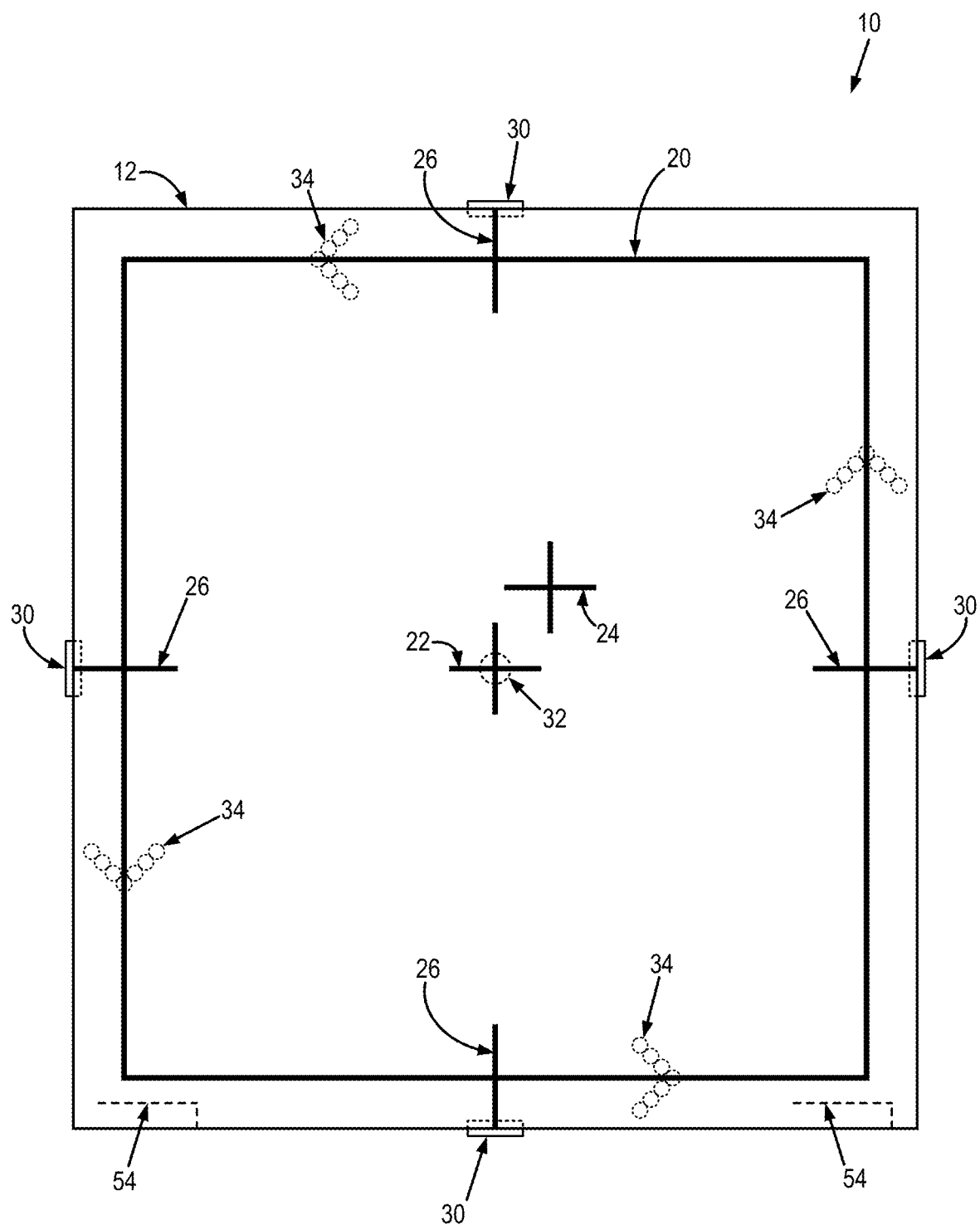
FIG. 3 is a top view of the example SNAP phantom of FIG. 1.

As one example, each of the one or more radiation FOV markers 34 can include a plurality of smaller radiopaque markers arranged to form a shape that indicates an orientation of the QA phantom 10. For instance, as shown in FIG. 3, each of the one or more radiation FOV markers 34 can include a plurality of cylindrical or spherical markers arranged in a V-shape. In this example, the cylindrical or spherical markers are coplanar and arranged within a plane that is parallel to the bottom surface 16 of the QA phantom 10 body 12. In this way, the orientation of the QA phantom 10 can be further verified based on the orientation of the V-shaped arrangement formed by the one or more radiation FOV markers 34. In the example shown in FIG. 3, the apex of each V-shaped arrangement of cylindrical or spherical markers is arranged on the boundary of the radiation FOV verification area, and different ones of the V-shaped arrangements are oriented to point in different directions. In other configurations, the one or more radiation FOV markers 34 can be differently aligned or arranged with respect to the radiation FOV verification area.

Whether a single marker or a plurality of markers, the one or more radiation FOV markers 34 can be sized and shaped as desired. Preferably, the radiation FOV markers 34 are sized and shaped so as to be readily identifiable by image analysis software, yet small enough so as not to interfere with the isocenter marker 30 or any other radiopaque markers.

Figure 4:
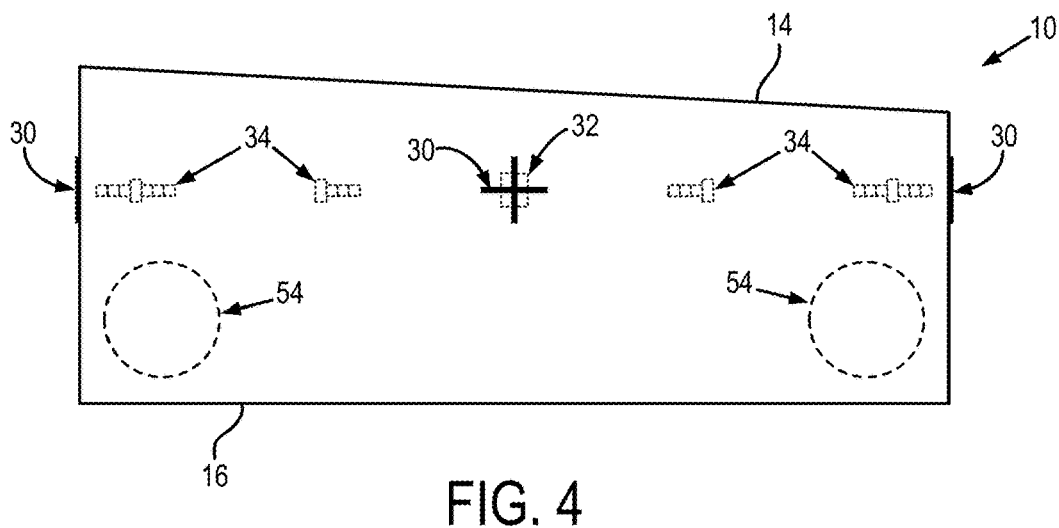
FIG. 4 is a front view of the example SNAP phantom of FIG. 1.
Figure 5:
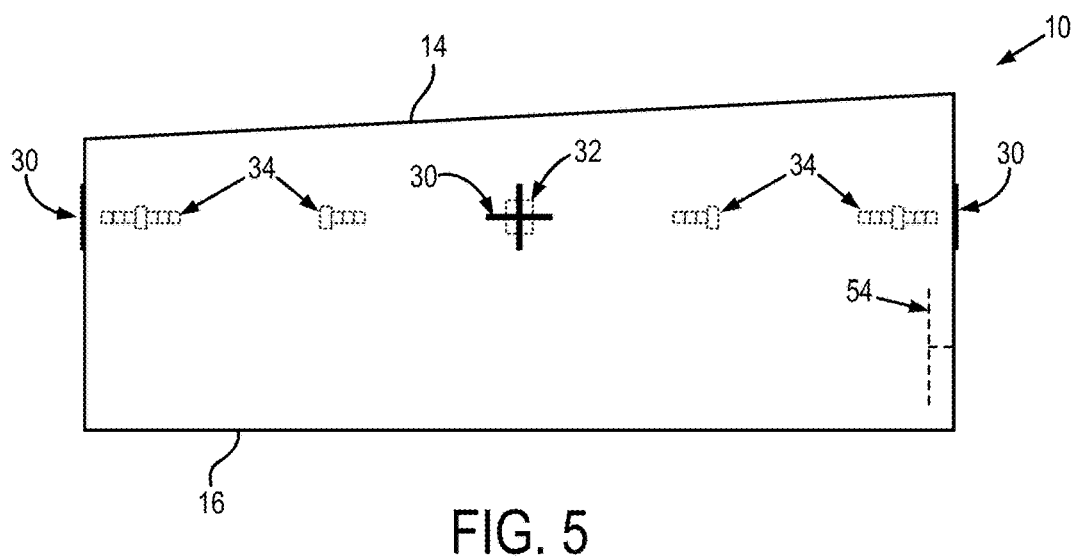
FIG. 5 is a right-side view of the example SNAP phantom of FIG. 1.
Figure 6:
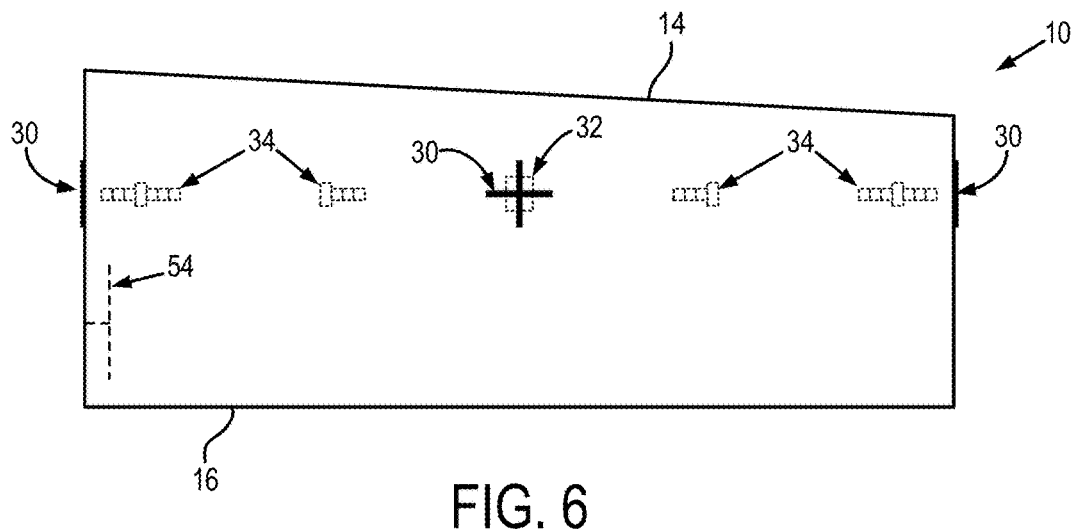
FIG. 6 is a left-side view of the example SNAP phantom of FIG. 1.

The radiation FOV markers 34 can be arranged within a plane that is parallel with the bottom surface 16 of the QA phantom 10 body 12, as shown for instance in FIGS. 4-6. Additionally or alternatively, the one or more radiation FOV markers 34 can be contained within a plane that is oblique relative to the bottom surface 16 of the QA phantom 10 body 12. Additionally or alternatively, the one or more radiation FOV markers 34 can be contained in more than one plane. For instance, the one or more radiation FOV markers 34 may include multiple markers, with one or more of such markers being arranged in different axial planes (e.g., planes parallel with the bottom surface 16 of the QA phantom 10 body 12).

In general, the one or more radiation FOV markers 34 can be arranged so as to be depicted in a single image of the QA phantom 10. For instance, when an x-ray projection image (e.g., a digital radiograph, portal image) of the QA phantom 10 is obtained, the one or more radiation FOV markers 34 may not need to be coplanar or in a plane parallel with the bottom surface 16 of the QA phantom 10 body 12.

As one example, the one or more radiation FOV markers 34 can demarcate a square-shaped radiation FOV verification area. For instance, the radiation FOV verification area can be a 15 cm-by-15 cm square. As another example, the one or more radiation FOV markers 34 can demarcate a radiation FOV verification area that is rectangular, circular, or any other polygonal or arbitrary shape.

Figure 9:
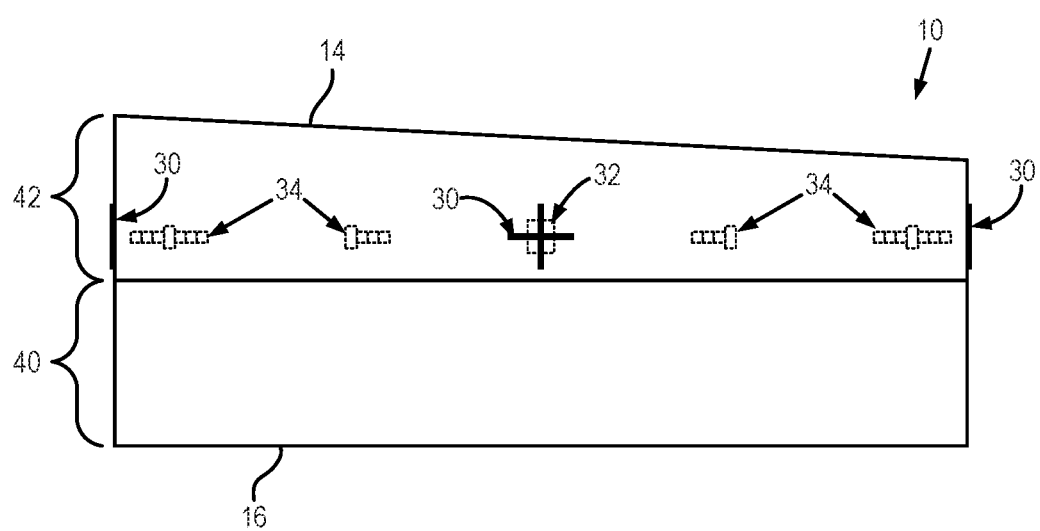
FIG. 9 is an example of a SNAP phantom having a phantom body composed of a base portion and an upper portion.

In some configurations, such as those shown in FIG. 9, the body 12 can be composed of a base portion 40 and an upper portion 42. In these instances, the radiopaque markers can be arranged in the upper portion 42 with no radiopaque markers in the base portion 40. The base portion 40 can thus be sized so as to separate the radiopaque markers from the treatment couch by a separation distance. The separation distance can be selected to avoid image artifacts that may occur when imaging the QA phantom 10 through the treatment couch at an angle. The separation distance (e.g., the height of the base portion 40) may be, for example, 3 cm. Alternatively, the separation distance can be greater than 3 cm.

As noted above, the top surface 14 of the body 12 is sloped and the angle of the slope is selected based on the pitch and roll specifications of the radiation treatment system or treatment couch. In some configurations where the body 12 of the QA phantom 10 is composed of a base portion 40 and an upper portion 42, the upper portion 42 may be removable from the base portion 40, such that upper portions 42 with a different top surface 14 slope, different top surface 14 markings, different radiopaque markers, or combinations thereof, can be interchangeable with the base portion 40. In this way, the QA phantom 10 can be adapted for use with different radiation treatment systems or treatment couches having different pitch and roll specifications.

In other configurations, the body 12 can be composed of a single piece. The radiopaque markers are then preferably arranged such that all of the radiopaque markers are positioned a minimum height above the bottom surface 16 of the body 12. As an example, this minimum height may be 3 cm. In still other configurations, the body 12 may be composed of more than two portions. In any such configuration, it may be preferable to have the radiopaque markers positioned above a minimum height from the bottom surface 16 of the body 12 (e.g., 3 cm or otherwise).

Figure 7:
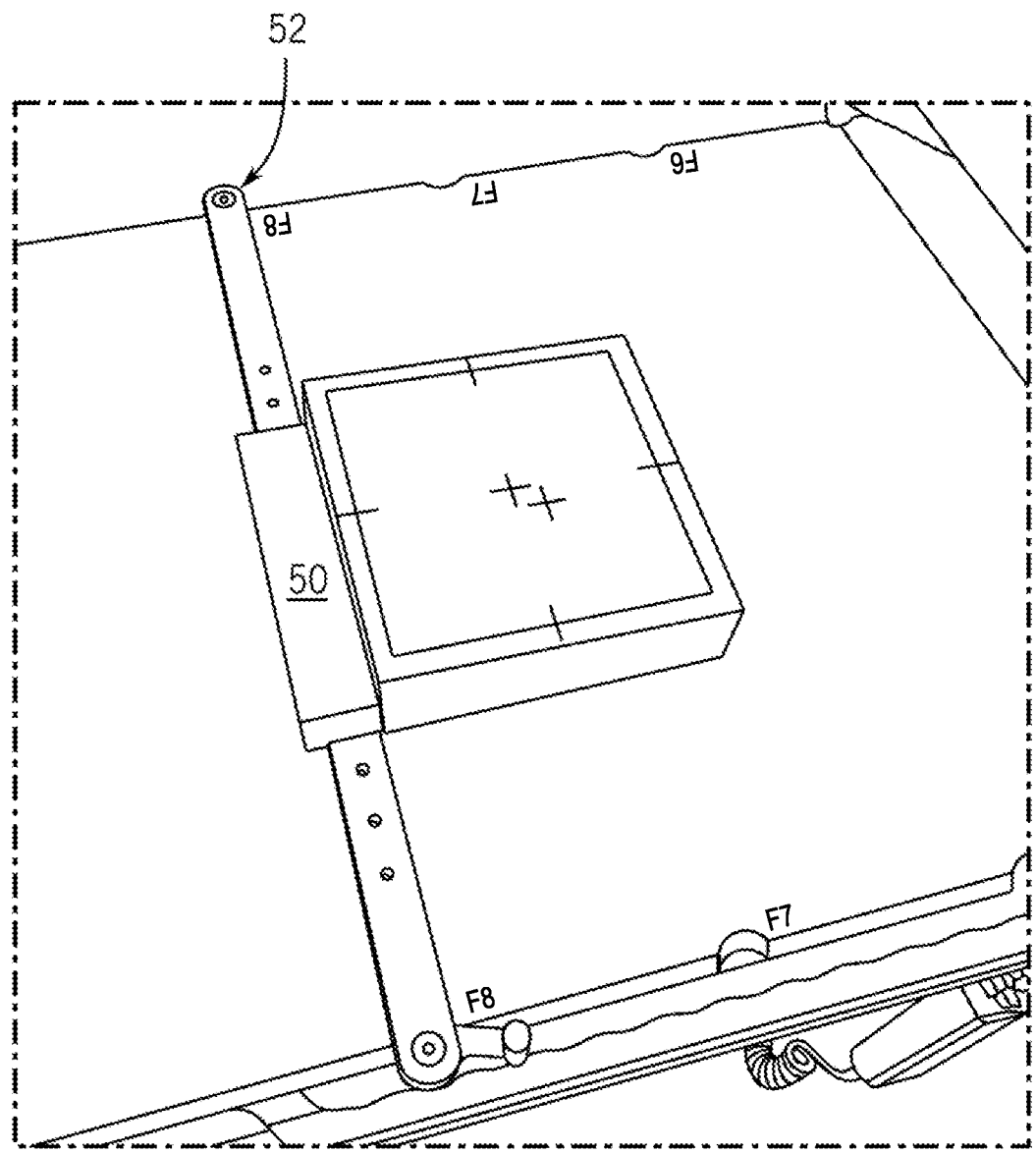
FIG. 7 is an example of a SNAP phantom positioned on a treatment couch of a radiation treatment system and coupled to an index bar via an adapter that is coupled to the side of the SNAP phantom.
Figure 8:
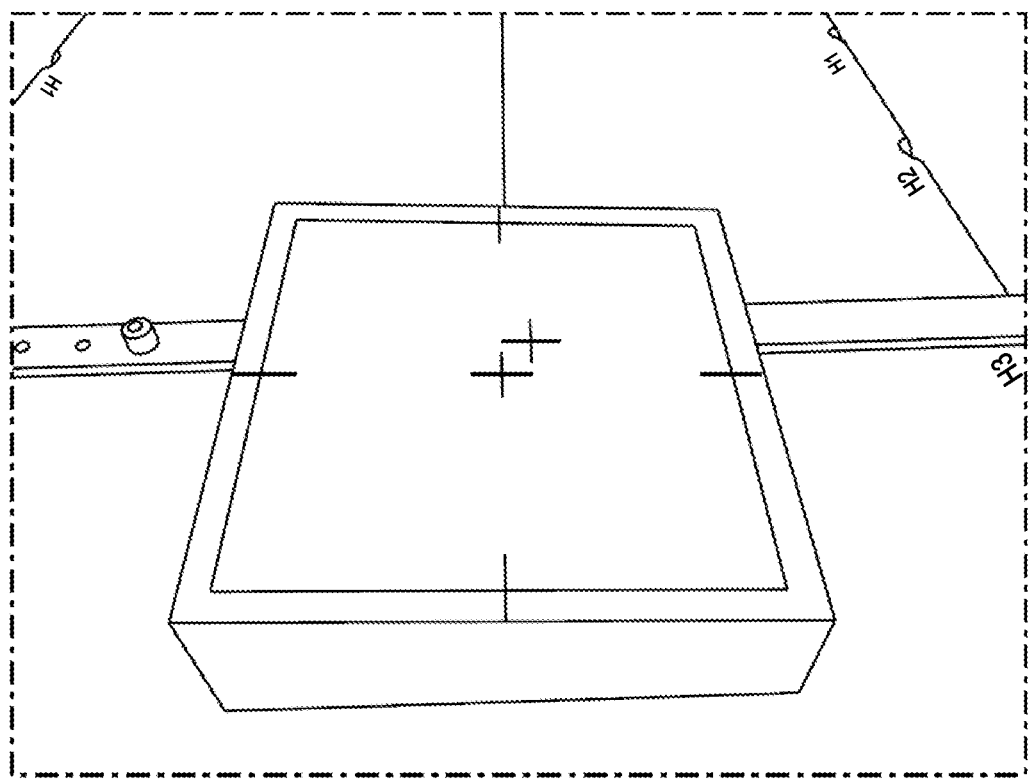
FIG. 8 is an example of a SNAP phantom positioned on a treatment couch of a radiation treatment system.

An adapter 50 for coupling the QA phantom 10 to an index bar 52 can be arranged along the edge 18 of the QA phantom 10 body 12, as shown in FIG. 7. The adapter 50 may be coupled to the edge 18 via slots 54 formed in the edge 18 (e.g., one or more sides of the QA phantom 10 body 12) or using other suitable connections or connectors. The adapter 50 enables the use of a standard index bar 52 for consistent and accurate placement of the QA phantom 10 while keeping the index bar out of the field-of-view of images obtained of the QA phantom 10. As one example, the adapter 50 can include a horizontal body that spans all or a portion of an edge 18 of the QA phantom 10 body 12. The adapter 50 can have a bottom surface that is partially recessed to define a notch. The notch is sized to receive an index bar. The adapter 50 can be coupled to the index bar when the index bar is arranged within the notch. As one example, the adapter 50 can be coupled to the index bar via pins or pegs coupling the adapter 50 to holes formed in the index bar.

Figure 10:
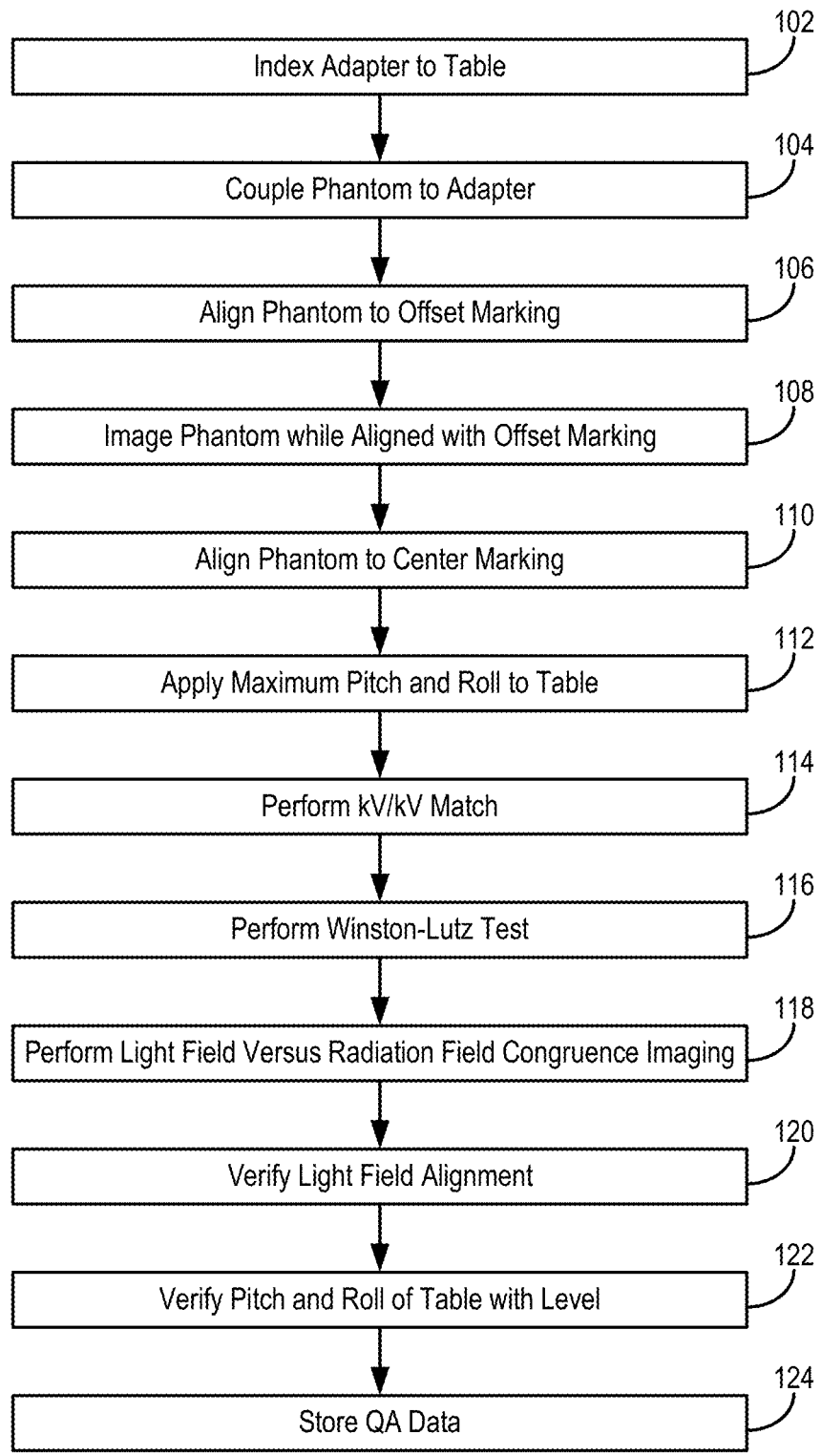
FIG. 10 is a flowchart setting forth the steps of an example method for implementing a quality assurance program of a radiation treatment system using a SNAP phantom.

Referring now to FIG. 10, a flowchart is illustrated as setting forth the steps of an example method for implementing a QA program using a QA phantom as described in the present disclosure. The method includes indexing the adapter to the table (i.e., treatment couch), as indicated at step 102. Next, the phantom is attached or otherwise coupled to the adapter, as indicated at step 104. The phantom is then aligned to the offset marking on the top surface of the phantom, as indicated at step 106. When aligned with the offset marking, the phantom is imaged, as indicated at step 108. For instance, the phantom can be imaged with and x-ray imaging system that forms a part of the radiation treatment system, such as a cone beam computed tomography ("CT") system. In some implementations, a portal imaging system may also be used.

The phantom is then aligned to the center marking on the top surface of the phantom, as indicated at step 110. When aligned with the center marking, the maximum pitch and roll shifts are applied to the table (i.e., treatment couch), as indicated at step 112. The shifts and the table position can be recorded as the absolute table position.

A planar kV/kV match is performed to check the coincidence with the cone beam CT system, as indicated at step 114. A MV Winston-Lutz test is then performed to check the coincidence with the other imaging systems and the radiation isocentricity, as indicated at step 116. Light field versus radiation field (e.g., x-ray) congruence imaging is performed, as indicated at step 118. The light field alignment is then verified relative to the markings on the top surface of the phantom, as indicated at step 120. The pitch and roll of the table are then verified by positioning a level on the top surface of the phantom while the table is in the absolute position (i.e., while the maximum pitch and roll shifts are applied), as indicated at step 122.

The data measured and recorded in these steps is then stored as QA data for later use by the medical physicist or other user, as indicated at step 124. For instance, the QA data can be used for logging the QA testing of the radiation treatment system, for guiding repairs or maintenance of the radiation treatment system, and so on. Thus, in some embodiments, a report may be generated based on the QA data.

The present disclosure has described one or more preferred embodiments, and it should be appreciated that many equivalents, alternatives, variations, and modifications, aside from those expressly stated, are possible and within the scope of the invention.

The invention claimed is:

1. A phantom for quality assurance of a radiation treatment system, comprising:
    a body having a top surface and a bottom surface, the body extending from the top surface to the bottom surface to define a volume, wherein the top surface is sloped relative to the bottom surface and wherein the body is composed of a radiotransparent material;
    a plurality of markings on the top surface of the body, comprising:
        a center marking located at a center of the top surface;
        an offset marking that is offset from the center marking;
        a field-of-view marking centered about the center marking and demarcating a field-of-view verification area for a light field of a radiation treatment system;
    a plurality of isocenter alignment markers arranged on an edge of the body;
    a plurality of radiopaque markers arranged within the volume of the body, comprising:
        an isocenter marker arranged within the volume of the body and centered with respect to the center marking; and a radiation field-of-view marker arranged about the isocenter marker to demarcate a field-of-view verification area for a radiation field of a radiation treatment system.

2. The phantom of claim 1, wherein the top surface of the body is sloped in a first direction by a first angle, and in a second direction by a second angle.

3. The phantom of claim 2, wherein the first angle corresponds to a pitch angle of a radiation treatment system for which the phantom is designed, and the second angle corresponds to a roll angle of the radiation treatment system for which the phantom is designed.

4. The phantom of claim 1, wherein the bottom surface of the body has a square shape.

5. The phantom of claim 1, wherein the field-of-view marking is aligned with the radiation field-of-view marker, such that the field-of-view verification area for the light field of the radiation treatment system is aligned with the field-of-view verification area for the radiation field of the radiation treatment system.

6. The phantom of claim 1, wherein the isocenter marker comprises one of a spherical marker or a cylindrical marker.

7. The phantom of claim 1, wherein the isocenter marker and the plurality of isocenter alignment markers are coplanar.

8. The phantom of claim 7, wherein the radiation field-of-view marker is coplanar with the isocenter marker and the plurality of isocenter alignment markers.

9. The phantom of claim 1, wherein each of the plurality of isocenter alignment markers are protrusions formed on the edge of the body.

10. The phantom of claim 1, wherein the radiation field-of-view marker comprises a plurality of radiation field-of-view markers that demarcate the field-of-view verification area for the radiation field of the radiation treatment system.

11. The phantom of claim 10, wherein each of the plurality of radiation field-of-view markers are oriented differently within the volume of the body and are shaped so as to uniquely indicate an orientation of the radiation field-of-view marker.

12. The phantom of claim 1, further comprising an adapter coupled to an edge of the body and configured to couple the body to an index bar.

13. The phantom of claim 1, wherein the body comprises a base portion and an upper portion arranged on top of the base portion, wherein the bottom surface of the body corresponds to a bottom surface of the base portion and the top surface corresponds to a top surface of the upper portion.

14. The phantom of claim 13, wherein the upper portion is removably coupled to the base portion such that the upper portion can be interchanged with another upper portion having a top surface with a different slope.

15. The phantom of claim 13, wherein the plurality of radiopaque markers are all contained within a volume of the upper portion.

16. The phantom of claim 15, wherein the base portion has a height that is selected to maintain a minimum separation distance between a treatment couch and the plurality of radiopaque markers.

17. The phantom of claim 16, wherein the minimum separation distance is 3 cm.

18. A phantom for quality assurance of a radiation treatment system, comprising:
a body having a top surface and a bottom surface, the body extending from the top surface to the bottom surface to define a volume;
wherein the top surface is sloped relative to the bottom surface in a first direction by a first angle, and relative to the bottom surface in a second direction by a second angle;
wherein the body is composed of a radiotransparent material;
wherein the first angle corresponds to a pitch angle of a radiation treatment system for which the phantom is designed, and the second angle corresponds to a roll angle of the radiation treatment system for which the phantom is designed; and
wherein the first angle is three degrees and the second angle is three degrees.

19. A phantom for quality assurance of a radiation treatment system comprising:
a body having a top surface and a bottom surface, the body extending from the top surface to the bottom surface to define a volume;
a plurality of markings on the top surface of the body, comprising:
a center marking located at a center of the top surface;
an offset marking that is offset from the center marking;
wherein the top surface is sloped relative to the bottom surface in a first direction by a first angle and relative to the bottom surface in a second direction by a second angle; and
wherein the body is composed of a radiotransparent material.

20. The phantom of claim 19, wherein the plurality of markings further comprises a field-of-view marking centered about the center marking and demarcating a field-of-view verification area for a light field of a radiation treatment system.

21. A phantom for quality assurance of a radiation treatment system comprising:
a body having a top surface and a bottom surface, the body extending from the top surface to the bottom surface to define a volume;
an isocenter marker arranged within the volume of the body and centered with respect to the center marking;
wherein the top surface is sloped relative to the bottom surface in a first directin by a first angle, and relative to the bottom surface in a second direction by a second angle; and
wherein the body is composed of a radiotransparent material.

22. The phantom of claim 21, further comprising a radiation field-of-view marker arranged about the isocenter marker to demarcate a field-of-view verification area for a radiation field of a radiation treatment system.

23. The phantom of claim 22, wherein the radiation field-of-view marker comprises a plurality of radiation field-of-view markers that demarcate the field-of-view verification area for the radiation field of the radiation treatment system.

* * * * *